US007328066B1

(12) United States Patent
Levine

(10) Patent No.: US 7,328,066 B1
(45) Date of Patent: Feb. 5, 2008

(54) IMPLANTABLE CARDIAC STIMULATION DEVICE, SYSTEM AND METHOD THAT IDENTIFIES AND PREVENTS IMPENDING ARRHYTHMIAS OF THE ATRIA

(75) Inventor: Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 450 days.

(21) Appl. No.: 10/401,497

(22) Filed: Mar. 28, 2003

(51) Int. Cl.
  - *A61N 1/08* (2006.01)
  - *A61B 5/0456* (2006.01)
  - *A61B 5/0472* (2006.01)

(52) U.S. Cl. .................. 607/25; 600/515; 600/516; 600/517

(58) Field of Classification Search ............... 600/510, 600/515–518; 607/4–28
See application file for complete search history.

(56) References Cited

U.S. PATENT DOCUMENTS

| | | | | |
|---|---|---|---|---|
| 4,365,639 A | | 12/1982 | Goldreyer | 128/786 |
| 4,869,252 A | * | 9/1989 | Gilli | 607/4 |
| 5,042,497 A | * | 8/1991 | Shapland | 600/509 |
| 5,144,947 A | * | 9/1992 | Wilson | 607/15 |
| 5,203,326 A | * | 4/1993 | Collins | 607/4 |
| 5,240,009 A | | 8/1993 | Williams | 128/702 |
| 5,441,523 A | * | 8/1995 | Nappholz | 607/14 |
| 5,560,368 A | | 10/1996 | Berger | 128/703 |
| 5,718,242 A | | 2/1998 | McClure et al. | 128/704 |
| 5,792,065 A | * | 8/1998 | Xue et al. | 600/516 |
| 5,899,866 A | * | 5/1999 | Cyrus et al. | 600/510 |
| 5,899,929 A | | 5/1999 | Thompson et al. | 607/28 |
| 5,916,239 A | | 6/1999 | Geddes et al. | 607/14 |
| 6,058,328 A | * | 5/2000 | Levine et al. | 607/14 |
| 6,134,470 A | * | 10/2000 | Hartlaub | 607/14 |
| 6,272,377 B1 | | 8/2001 | Sweeney et al. | 600/515 |
| 6,292,694 B1 | | 9/2001 | Schloss et al. | 607/9 |
| 6,353,757 B2 | | 3/2002 | Chen | 607/3 |
| 6,370,431 B1 | * | 4/2002 | Stoop et al. | 607/14 |
| 6,398,800 B2 | | 6/2002 | Chen | 607/1 |
| 6,400,982 B2 | | 6/2002 | Sweeney et al. | 600/515 |
| 6,438,410 B2 | * | 8/2002 | Hsu et al. | 600/516 |
| 6,480,742 B2 | * | 11/2002 | Stahmann et al. | 607/27 |
| 6,516,219 B1 | * | 2/2003 | Street | 600/515 |
| 6,539,260 B1 | * | 3/2003 | Schloss | 607/9 |
| 6,606,517 B1 | * | 8/2003 | Park et al. | 607/14 |
| 2001/0020136 A1 | | 9/2001 | Sweeney et al. | 600/515 |
| 2002/0016550 A1 | | 2/2002 | Sweeney et al. | 600/515 |
| 2002/0029002 A1 | * | 3/2002 | Bardy | 600/518 |
| 2002/0091330 A1 | * | 7/2002 | MacAdam et al. | 600/509 |
| 2003/0014083 A1 | * | 1/2003 | Kupper | 607/9 |

(Continued)

FOREIGN PATENT DOCUMENTS

EP     0547734 A2     6/1993

(Continued)

*Primary Examiner*—Carl Layno
*Assistant Examiner*—Tammie K Heller

(57) ABSTRACT

An implantable cardiac stimulation device includes a system that identifies and prevents the occurrence of impending atrial arrhythmias. A sensing circuit senses atrial activity of a patient's heart to provide an atrial activity signal. A processor compares the atrial activity signal to a predetermined standard indicative of an impending accelerated atrial arrhythmia to identify an impending accelerated atrial arrhythmia. A therapy circuit provides accelerated atrial arrhythmic preventive therapy to the patient when an impending accelerated atrial arrhythmia is identified. Data associated with the identification and therapy delivery is stored in a memory.

30 Claims, 5 Drawing Sheets

U.S. PATENT DOCUMENTS

2003/0097156 A1* 5/2003 Henry et al. .................... 607/9
2004/0127950 A1* 7/2004 Kim et al. ..................... 607/27

FOREIGN PATENT DOCUMENTS

| | | | |
|---|---|---|---|
| EP | 0547734 | A3 | 6/1993 |
| EP | 0547734 | B1 | 4/1998 |
| WO | WO 01/24876 | A1 | 4/2001 |
| WO | WO 01/62334 | A2 | 8/2001 |
| WO | WO 01/62334 | A3 | 8/2001 |
| WO | WO 02/34123 | A2 | 5/2002 |
| WO | WO 02/34123 | A3 | 5/2002 |

* cited by examiner

IMPLANTABLE CARDIAC STIMULATION DEVICE, SYSTEM AND METHOD THAT IDENTIFIES AND PREVENTS IMPENDING ARRHYTHMIAS OF THE ATRIA

FIELD OF THE INVENTION

The present invention generally relates to an implantable cardiac stimulation device, system and method that identifies impending accelerated atrial arrhythmias. The present invention further relates to such a device, system and method wherein atrial arrhythmia prevention therapy is applied to the heart when an impending accelerated atrial arrhythmia substrate is identified.

BACKGROUND OF THE INVENTION

Atrial fibrillation is a common arrhythmia becoming increasingly frequent as patients advance in age. It is associated with a multiplicity of symptoms including fatigue, weakness, syncope, congestive heart failure, and strokes. It is a major cause of hospitalizations and of morbidity resulting in a significant economic burden to the individual and society.

Numerous therapies have been advanced to terminate accelerated atrial arrhythmias such as atrial fibrillation or organized atrial tachyarrhythmias such as atrial flutter. For example, high rate or overdrive pacing of the atria has shown to be effective in some cases to terminate atrial flutter. For atrial arrhythmias which advance to the more chaotic atrial fibrillation, overdrive pacing may still be effective in some cases. Atrial defibrillation, which entails delivering a brief cardioverting electrical shock to the atria, has also been found to be effective in some cases.

Before a therapy can be delivered, the arrhythmia itself must first be detected. Generally, such detection involves the sensing of high rate intrinsic atrial beats, whether they are normal (slight acceleration of a normal sinus rhythm) or premature and ectopic. However, such detection is not totally effective and even when found to work well in a given patient, rate changes alone may not be an adequate precursor in every instance. This suggests that there is more that is transpiring at the atrial muscle layer or cellular level than has been identified to date. If the earliest precursors are missed, later therapy may be inadequate to terminate the arrhythmia.

It has been shown that the longer that patients are in normal sinus rhythm, the more likely it is that they will stay in normal sinus rhythm. Hence, it would be most advantageous if an impending accelerated atrial arrhythmia could be identified and then upon such identification, preventative therapy delivered to the patient to keep the patient's atrial arrhythmia from developing and maintaining the patient in normal sinus or stable atrial paced rhythm. The present invention addresses these issues.

SUMMARY

The present invention provides, a system for use in a cardiac stimulation device that identifies and prevents the occurrence of impending atrial arrhythmias in a patient. The system includes a sensing circuit that senses atrial activity of a patient's heart and provides an atrial activity signal, a processor that compares at least one characteristic of the atrial activity signal to a predetermined standard of the at least one characteristic indicative of an impending accelerated atrial arrhythmia to identify an impending accelerated atrial arrhythmia, a therapy circuit responsive to the processor identifying an impending accelerated atrial arrhythmia that provides accelerated atrial arrhythmia preventive therapy to the patient, and a memory that stores data associated with the impending accelerated atrial arrhythmia identification and preventive therapy delivery.

Preferably, the sensing circuit senses the atrial activity during a window or predetermined portion of each cardiac interval. In one illustrative embodiment, the window is set to coincide with an atrial repolarization signal (hereinafter referred to as an "atrial T wave"). The at least one characteristic may be one of atrial T wave amplitude, atrial T wave morphology, P wave to atrial T wave interval, and A stimulus to atrial T wave interval.

The processor is preferably arranged to provide a template of the at least one characteristic correlated over time with impending accelerated atrial arrhythmias. The processor may then compare the atrial activity signal to the template and identify an impending accelerated arrhythmia when the atrial activity signal falls within the template. The processor may further be arranged to provide a first template including the at least one characteristic and a second template including the at least one characteristic, wherein one of the templates corresponds to intrinsic atrial activity and the other template corresponds to paced atrial activity. The processor may further be arranged to classify the sensed atrial activity as one of intrinsic and paced activity and to compare the sensed atrial activity with a corresponding one of the first and second templates.

The therapy circuit may be arranged to provide preventative therapy taking the form of high rate atrial pacing or extra cardiac stimulation. For example, the therapy circuit may be arranged to provide stimulation pulses to the stellate ganglia of the patient.

The data to be stored in memory may include the time and date of each identification of an accelerated atrial arrhythmia. The data may further include the duration of therapy and the time interval between identifications. The processor may be arranged to determine the effectiveness of the therapy at returning the at least one characteristic to within a preset standard and the data may thus include an indication of the patient's response to the therapy. The response may be indicative of effectiveness and ineffectiveness. The therapy circuit may further be arranged to increase therapy aggressiveness when therapy is ineffective.

The present invention still further provides a cardiac stimulation device comprising sensing means for sensing atrial activity of a patient's heart and providing an atrial activity signal and processing means for comparing at least one characteristic of the atrial activity signal to a predetermined standard of the at least one characteristic indicative of an impending accelerated atrial arrhythmia to identify an impending accelerated atrial arrhythmia. The device may further include therapy means responsive to the processing means identifying an impending accelerated atrial arrhythmia for providing accelerated atrial arrhythmia preventive therapy to the patient and memory means for storing data associated with the impending accelerated atrial arrhythmia identification and preventive therapy delivery.

The present invention still further provides a method for use in a cardiac stimulation device which identifies and prevents the occurrence of impending atrial arrhythmias in a patient. The method includes the steps of sensing atrial activity of a patient's heart and providing a corresponding atrial activity signal, comparing at least one characteristic of the atrial activity signal to a predetermined standard of the at least one characteristic indicative of an accelerated atrial arrhythmia to identify an impending accelerated atrial arrhythmia, responsive to identifying an impending accelerated atrial arrhythmia, providing accelerated atrial arrhythmia preventive therapy to the patient, and storing in a memory data associated with the impending accelerated atrial arrhythmia identification and preventive therapy delivery.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
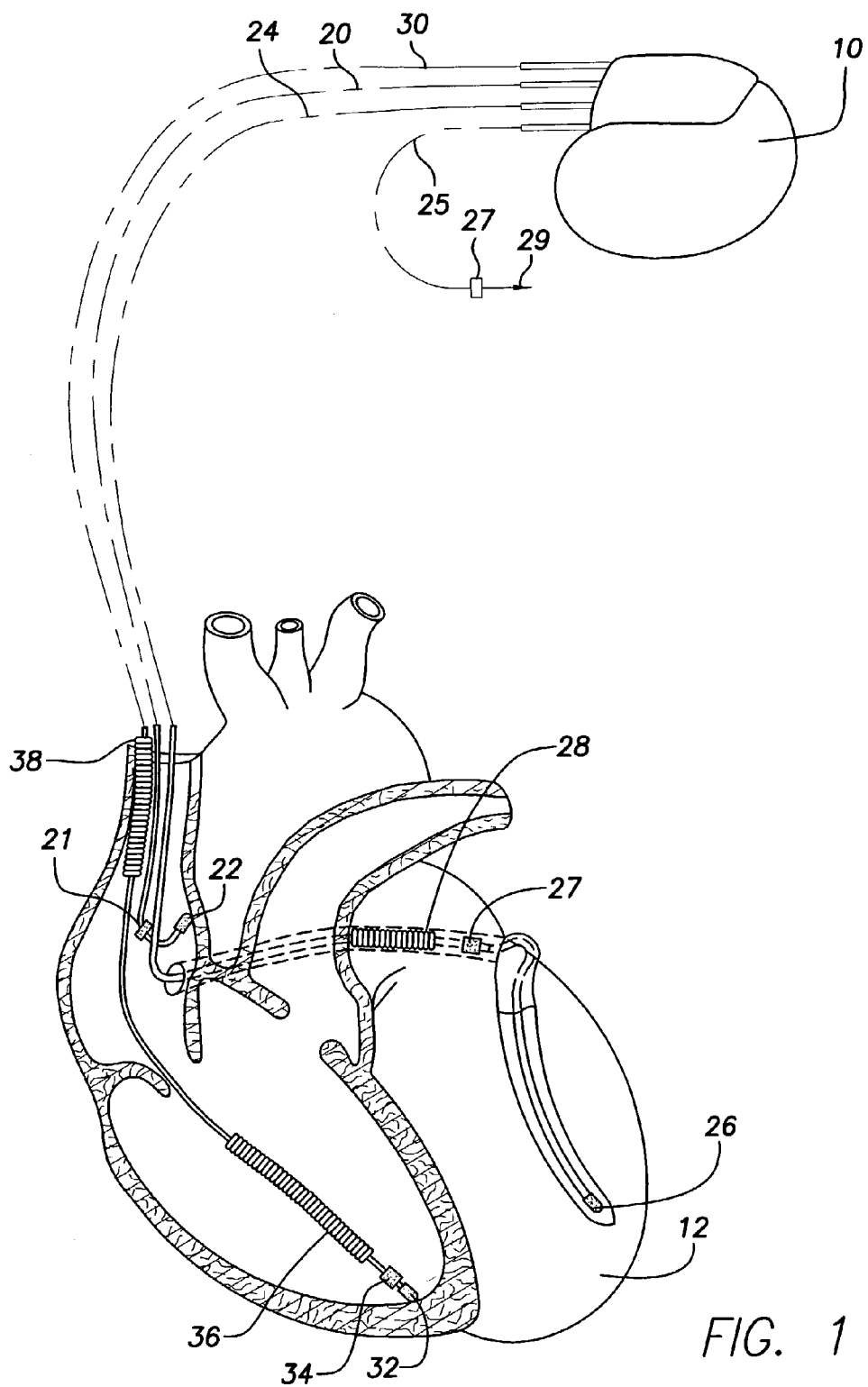
FIG. 1 is a simplified diagram illustrating an implantable stimulation device embodying the present invention.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial ring electrode 21 and an atrial tip electrode 22, which are typically implanted in the patient's right atrial appendage. The electrodes 21 and 22 form a bipolar electrode pair useful for right atrial pacing and near field targeted atrial activity sensing.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
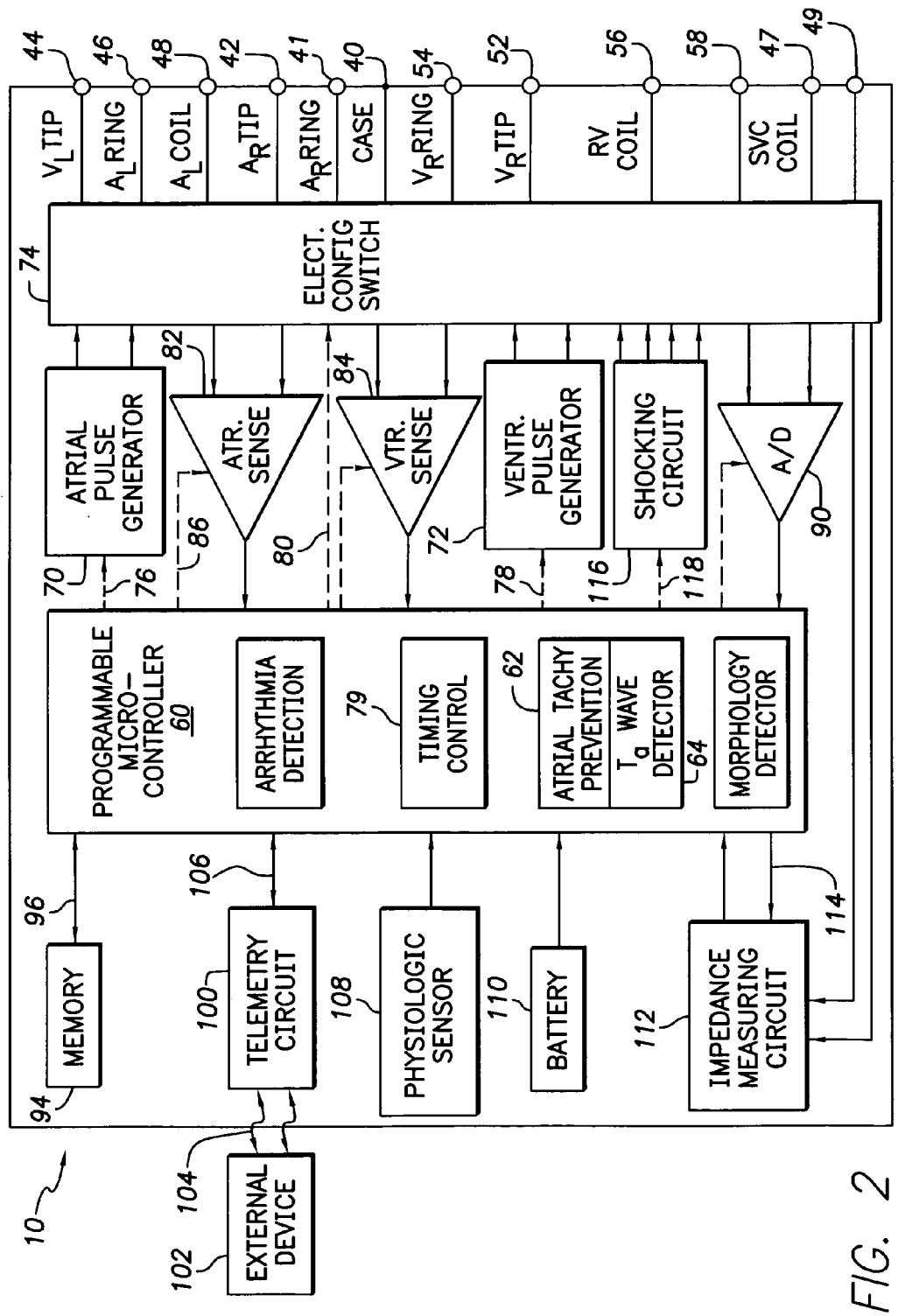
FIG. 2 is a functional block diagram of the implantable stimulation device of FIG. 1.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 41, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial ring terminal ($A_R$ RING) 41 and a right atrial tip terminal ($A_R$ TIP) 42 adapted for connection to the atrial ring and tip electrodes 21 and 22, respectively.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time (preferably less than 10 μA), and then be capable of providing high-current pulses (for capacitor charging) when the patient requires a shock pulse (preferably, in excess of 2 A, at voltages above 2 V, for periods of 10 seconds or more). The battery 110 must also have a predictable discharge characteristic so that elective replacement time can be detected. Accordingly, the device 10 may employ lithium/silver vanadium oxide batteries.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Now that the implantable cardiac stimulation device 10 has been generally described, this description will now turn to the aspects of the device 10 which more directly relate to this embodiment of the present invention. As previously noted, the present invention is directed to identifying an impending atrial accelerated arrhythmia and then providing therapy to the patient to preclude the impending arrhythmia from developing.

The identification of an impending accelerated atrial arrhythmia, in accordance with this embodiment, is accomplished by sensing localized atrial activity, generating an electrical signal corresponding to the sensed atrial activity, and comparing at least one characteristic of the signal to a predetermined standard indicative of an impending accelerated atrial arrhythmia. To sense the atrial activity, the device 10 employs the atrial bipolar electrodes 21 and 22 for sensing localized atrial activity. The electrodes 21 and 22 are coupled to the data acquisition system 90 which generates an electrical signal corresponding to the sensed atrial activity.

To implement the compare function, the microcontroller (processor) 60 includes an atrial tachycardia prevention stage 62 that processes the atrial activity signal to identify an impending accelerated atrial arrhythmia. To that end, the stage 62 develops a template of atrial T wave morphology, duration and/or amplitude over time correlated with impending accelerated atrial arrhythmias. This is performed for a number of atrial tachyarrhythmic episodes and separately for paced atrial T waves and intrinsic atrial T waves. The templates may be generated automatically or by command of the physician.

To generate the templates and to acquire the atrial activity signals, the data acquisition system 90 establishes a sensing window during each cardiac cycle. Information retrieved during this time period is preferably not used to increment any rate counter or alter delivered standard therapy. The window may overlap the early alert period in an atrial anti-tachyarrhythmia device since these periods are very short and the atrial T wave may fall within such an alert period. Hence, the atrial activity window should be chosen to encompass the entire atrial T wave. Hence, the paced beat template could include paced $T_a$ wave morphology, amplitude or shape, and/or atrial stimulation-$T_a$ interval (A-$T_a$ INTERVAL). Similarly, the intrinsic beat template will include $T_a$ amplitude, $T_a$ wave morphology or shape, and/or atrial activation-$T_a$ interval (P-$T_a$ INTERVAL). A particular template generating process will be described in connection with FIG. 4.

Utilizing these templates, the system continuously monitors the rhythm and various atrial T wave characteristics for a consistent response. This consistent response can be based on an absolute number of identical responses or "x" out of "y" similar or identical responses preceding the onset of a tachyarrhythmia. The T wave characteristics may be further characterized with respect to arrhythmias with different rates. For example, an atrial tachyarrhythmia at a rate of 200 bpm may have different preceding T wave characteristics than an atrial tachyarrhythmia at 250 bpm or 300 bpm. The T wave characteristics specific for each tachyarrhythmia can be stored in device memory and may be used to direct preventive therapy for the specific tachyarrhythmia. As further capabilities are incorporated, such as multiple leads allowing for a multiplicity of detection electrode configurations, the tachyarrhythmia can be further characterized and specified. The premonitory atrial T wave templates may be determined after a preset or programmable period of time such as weeks or months or a preset or programmable number of spontaneous tachycardia events.

Once the templates are generated, the atrial activity is sensed during normal operation of the device 10. The atrial T wave is extracted from the atrial activity signal by the $T_a$ wave detector 64 of the stage 62. At least one characteristic of the sensed paced or intrinsic $T_a$ wave is compared to the corresponding characteristic of the corresponding template. If a T wave characteristic, or a consistent number of them fall within the corresponding correlated template, the stage 62 will indicate that it has identified an impending accelerated atrial arrhythmia and will implement preventive therapy.

The preventive therapy may take the form of atrial overdrive pacing at single or multiple stimulation sites, as is known in the art or the stimulation of extra-cardiac tissue. For example, the stellate ganglia may be stimulation. This nerve, part of the sympathetic nervous system has been known to exhibit growth as a result of acute myocardial infarction. Stimulation of this nerve would block impulses to the heart which may be arrhythmogenic. To this end, as shown in FIG. 1, the device 10 includes a further lead 25 having a ring electrode 27 and a distal electrode 29 for delivering the stimulation to the stellate ganglia. The atrial pulse generator 70 may be used to generate the stimulus. The stimulus may then be coupled by the switch 74 to the terminals 47 and 49 coupled to electrodes 27 and 29 respectively.

During therapy delivery, therapy effectiveness is monitored. If the monitored characteristic returns to baseline, the therapy may be continued for a preset time and then terminated. If therapy is ineffective its aggressiveness (amplitude, duration, rate) may be increased. If the monitored characteristic then returns to baseline, the therapy may be gradually reduced until terminated. However, since this process is being performed separately from the normal functioning of the device, should the accelerated atrial arrhythmia develop, this would be detected by the device at which time the preventive therapy would end and the normal response to such a tachyarrhythmia would be initiated along with anti-arrhythmia therapy such as anti-tachycardia pacing or defibrillation would take place.

The foregoing provides an opportunity for logging data which would be valuable for the physician treating the patient with respect to future atrial arrhythmia. Hence, in accordance with the present invention, after therapy delivery is completed, data may be stored in memory 94 that is associated with the impending accelerated atrial arrhythmia identification and preventive therapy delivery. Such data may include the time and date of the identifications, the duration of the preventive therapeutic interventions and the response to the preventive therapy. Associated with the response may be stored an indication of the therapy effectiveness or ineffectiveness in returning the monitored characteristic to baseline. An indication may be stored, for example, indicating that there was no change in the monitored characteristic that resulted in more aggressive therapy and/or the development of the accelerated atrial arrhythmia requiring standard anti-tachycardia pacing or defibrillation. Further stored data may include the time interval between the impending arrhythmia identification/therapy delivery and the development of atrial tachycardia or atrial fibrillation that required standard intervention. This would provide the physician with additional information that the therapy was not successful or needed to be continued for a longer period of time.

Lastly, since atrial fibrillation and other tachyarrhythmias are not immediately life threatening, the physician may elect to withhold preventive therapy and only perform the impending arrhythmia identification and data storage. In the sole monitoring mode, it would not be possible to determine if the preventive therapy would have altered the course of events, but it would provide information whether the monitored event was a valid precursor for episodes of atrial tachycardia or atrial fibrillation occurring within a reasonable period of time. By then enabling therapy delivery, it may be determined if, in this same setting, the atrial tachycardia or atrial fibrillation could be prevented or delayed, and if delayed, to what degree. Hence it may be determined if a new episode occurred within minutes after cessation of therapy or hours later and if the occurrence at that time was again preceded by a period wherein the atrial T waves were unstable for which a second course of pacing was or was not effective.

Figure 3:
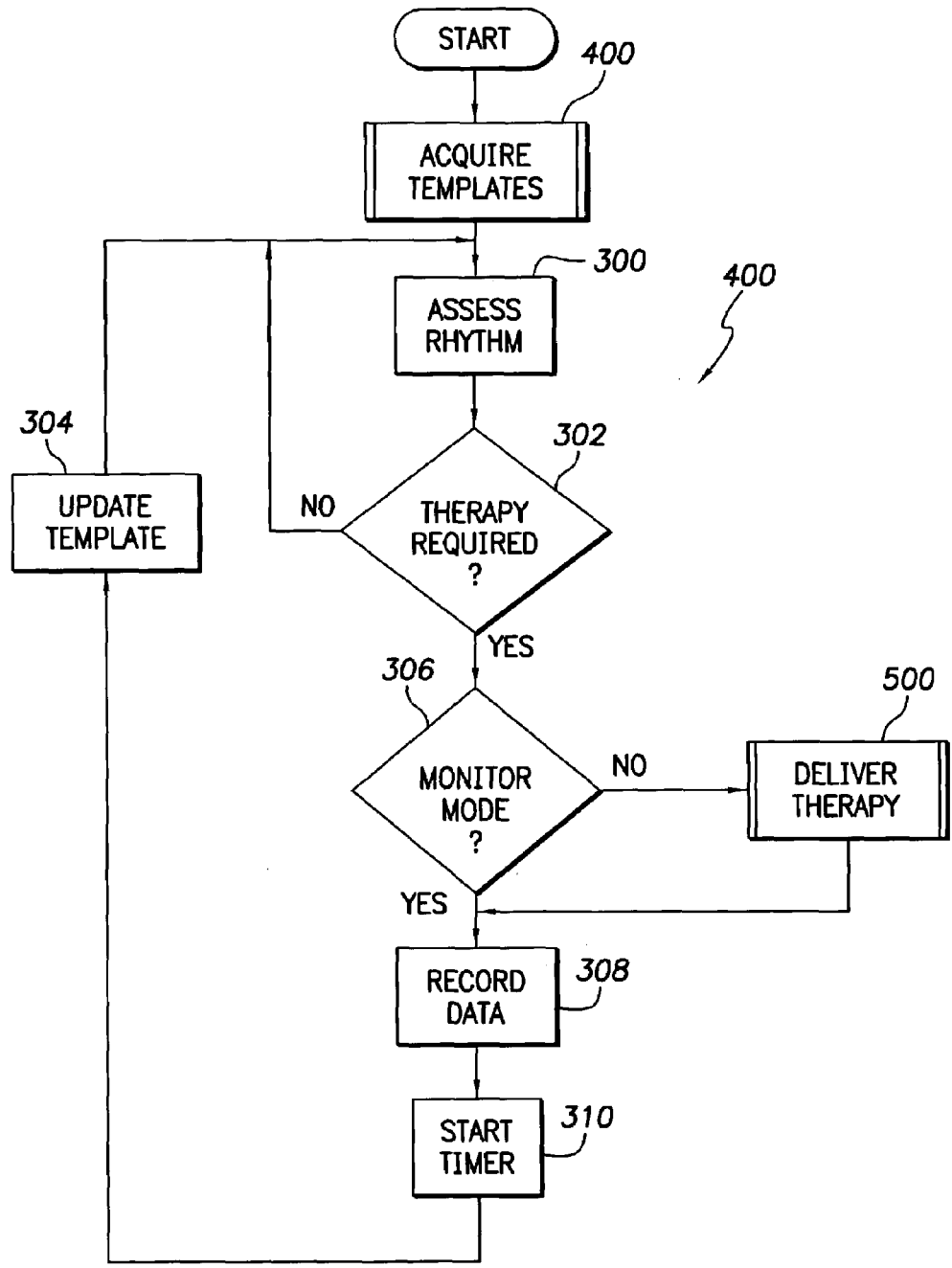
FIG. 3 is a flow chart describing an overview of the operation of one embodiment of the present invention.

In FIG. 3, a flow chart is shown describing an overview of the operation and novel features implemented in one embodiment of the device 10. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The overall implementation of this embodiment of the present invention initiates with a subroutine 400 wherein the atrial tachycardia prevention stage 62 acquires the atrial T wave templates. As previously mentioned, the stage 62 acquires a template for paced atrial beats and a template for intrinsic atrial beats. The manner in which the templates may be acquired is described more particularly hereinafter with reference to FIG. 4.

After the templates are acquired in accordance with the subroutine 400, the process advances to an activity block 300 wherein the atrial tachycardia prevention stage 62 assesses the atrial rhythm of each sensed cardiac cycle of the heart. In assessing each rhythm, the stage 62 determines whether the atrial beat is a paced beat or an intrinsic beat. After the atrial beat has been characterized in activity block 300, the process advances to decision block 302 wherein the stage 62 determines if preventive therapy is required. In implementing decision block 302, the stage 62 compares at least one characteristic in the atrial activity signal sensed in the sensing window of the data acquisition system 90 to a predetermined standard which is indicative of an impending accelerated atrial arrhythmia. As previously mentioned, the characteristic monitored and compared may be the atrial T wave amplitude, atrial T wave morphology, or the atrial event (sensed or paced) to atrial T wave interval. If a current monitored characteristic is significantly different than (falls outside of) the stored template, the stage 62 determines that therapy is not required and the process returns to activity block 300 for assessing the next atrial rhythm.

If in decision block 302 it is determined that the monitored characteristic (or a consistent number of them) is not significantly different than (falls within) the stored template, the atrial tachycardia prevention stage 62 declares that it has identified an impending accelerated atrial arrhythmia in need of preventive therapy. Before providing such therapy, however, the process advances to decision block 306 wherein it is determined if the device has been set in the monitor mode. If the device has been set in the monitor mode, preventive therapy is withheld. Following such a determination, the process advances to activity block 308 wherein data associated with the identification of the impending accelerated atrial arrhythmia is recorded in memory 94. That data may include the time and date of the identification of the impending accelerated atrial arrhythmia and the time since the last identified impending accelerated atrial arrhythmia. Once the requisite data has been stored in memory 94, the process advances to activity block 310 wherein a timer, such as may be included in timing control 79 of FIG. 2, to begin timing the time period to the next identified impending accelerated atrial arrhythmia. Following activity block 310, the process advances to activity block 304 to update the appropriate template and then returns to activity block 300.

If in decision block 306 it is determined that the device is not in the monitor mode, the process then advances to a subroutine 500 wherein preventive therapy is delivered to prevent the occurrence of the accelerated atrial arrhythmia. The preventive therapy may be specific for the anticipated atrial tachyarrhythmia based upon prior experience stored in device memory as previously described. Also as previously described, the preventive therapy may take the form of pacing the heart such as by atrial overdrive pacing or stimulation of extra-cardiac tissue such as the stellate ganglia, the parasympathetic ganglia, or the central nervous system of the patient. The therapy delivery subroutine 500 is described in greater detail hereinafter in connection with FIG. 5.

Once therapy delivery is completed in accordance with subroutine 500, the process then advances to the data recording activity block 308. In addition to the data recorded in the monitor mode, the data recorded following therapy delivery may further include duration of the therapeutic intervention and an indication of the response to the therapeutic intervention. The indication of the therapeutic response may indicate no change resulting in more aggressive intervention and/or lack of success with development of atrial tachycardia or atrial fibrillation requiring standard anti-tachycardia pacing or defibrillation therapy. Of course, the response indication may further include an indicia of success in that the abnormal characteristic returned to baseline. Therapy delivery also enables a further diagnostic parameter to be recorded in the form of the time interval between the identification of the accelerated atrial arrhythmia/therapy delivery and the development of atrial tachycardia or atrial fibrillation in need of standard intervention. As previously mentioned, this may provide the physician with additional information that the therapy was not successful or needed to be continued for a longer period of time.

Figure 4:
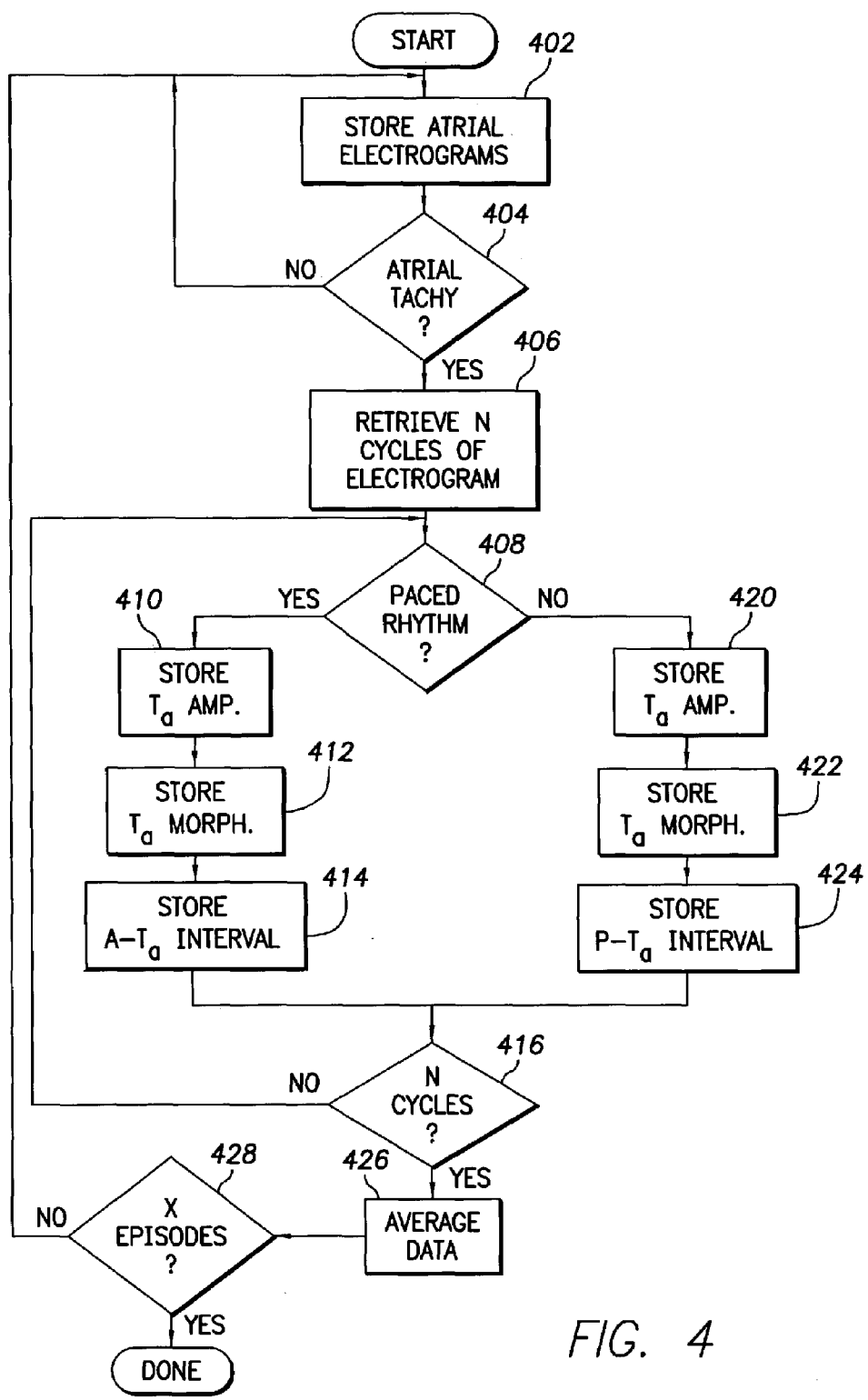
FIG. 4 is a flow chart describing the manner in which the template may be acquired in accordance with the present invention.

Referring now to FIG. 4, it illustrates the subroutine 400 of FIG. 3 for acquiring the atrial paced event and sensed event templates. The subroutine 400 initiates with an activity block 402 wherein the atrial tachycardia prevention stage 62 initiates sensing and storage of atrial electrograms by the data acquisition system 90. The electrograms may be of complete cardiac cycles or at least complete atrial T waves as previously described. As previously mentioned, the switch 74 couples the inputs of the data acquisition system 90 to the atrial ring electrode 21 and atrial tip electrode 22 for sensing localized atrial activity. This enables the atrial T waves to be sensed and stored.

Once the data acquisition system 90 begins sensing and storing atrial activity, the process advances to decision block 404 wherein it is determined if an accelerated atrial arrhythmia is present. This determination is made by the arrhythmia detector. If there is no accelerated atrial arrhythmia, the process returns. If there is an accelerated atrial arrhythmia, the process then advances to activity block 406 wherein the processor retrieves the last N cycles of atrial electrograms or atrial T waves. Once the atrial T waves are retrieved from memory, the process advances to decision block 408 to determine if the first T wave of the N T waves is from an atrial paced beat. If the T wave is from an atrial paced beat, the process advances to a series of activity blocks 410, 412, and 414 which are performed for each of the N number of cardiac cycles which are atrial paced beats. In the first activity block 410, the paced atrial T wave amplitude is stored. In activity block 412, the morphology or shape of the paced atrial T wave is stored. In the last activity block 414 the paced atrial event to the paced atrial T wave interval is stored.

Following activity block 414, the processor then determines, at decision block 416, if each of the N number of cardiac cycles have been processed. If not, the process then returns back to decision block 408 for processing the atrial T wave of the next cardiac cycle. If the next T wave is that of an intrinsic atrial beat, the process advances from decision block 408 to a series of activity blocks 420, 422, and 424. For each one of the predetermined number of consecutive cardiac cycles, the processor stores the sensed atrial T wave amplitude in activity block 420, the sensed atrial T wave morphology or wave shape in activity block 422, and the sensed atrial event to the sensed atrial T wave interval in activity block 424. After the predetermined number of cardiac cycles is completed, the data stored for each of the intrinsic and paced beats may be averaged in activity block 426 to derive the templates. Then in activity block 428 it is determined if this process has been repeated for a sufficient number X accelerated atrial episodes. If sufficient episodes have been processed, the process completes. If not, the process returns. Once completed, the stage 62 will have stored a number of templates correlated to impending atrial accelerated arrhythmias for use in detecting impending accelerated atrial arrhythmias.

Once the atrial paced event template and atrial sensed event template are acquired and stored in memory 94 by the atrial tachycardia prevention stage 62, the overall process continues then to assess the subsequent atrial rhythms for impending accelerated atrial arrhythmias. As will be noted from FIG. 3, during this process, for those cardiac cycles wherein preventive therapy is required, the appropriate template is updated.

Figure 5:
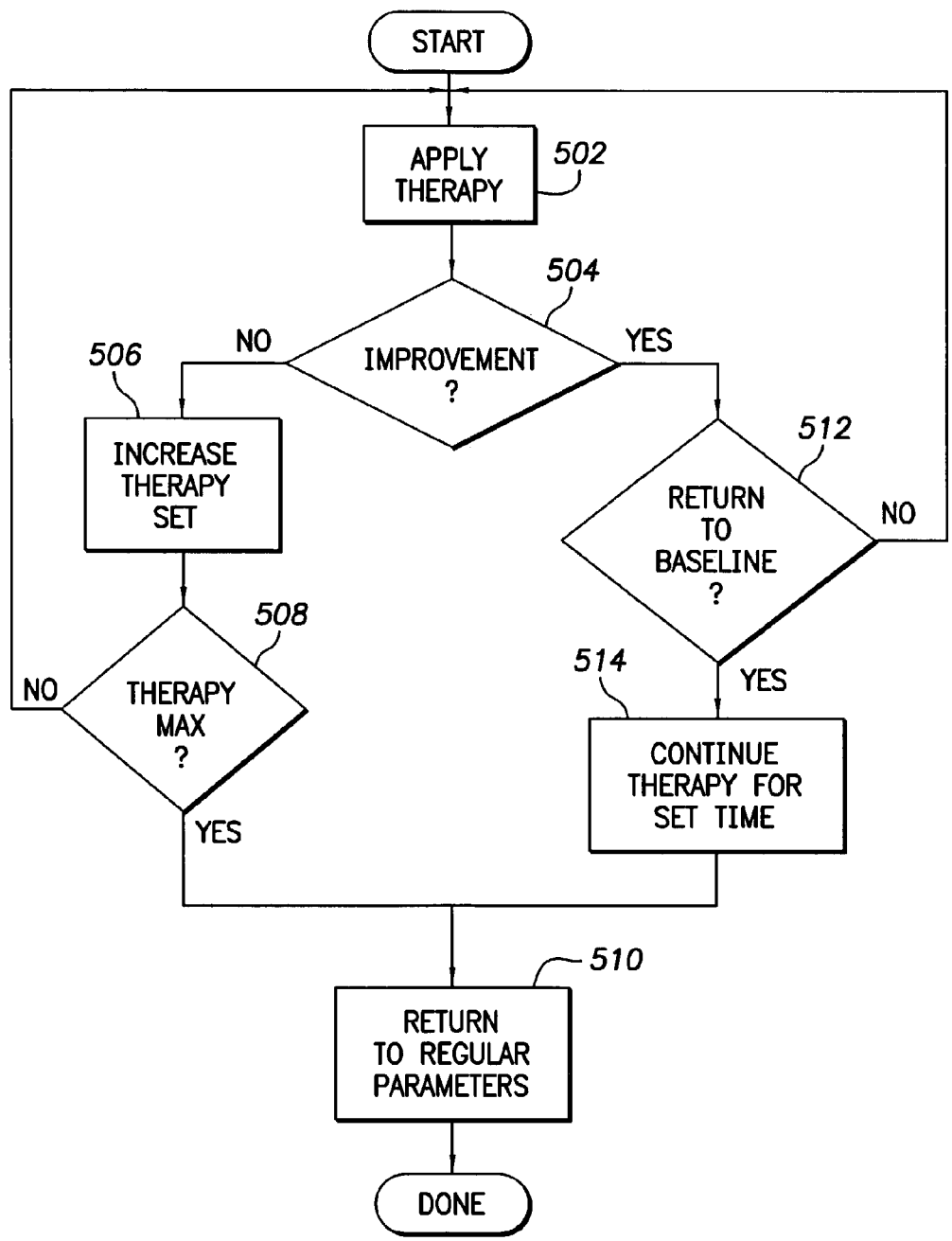
FIG. 5 is a flow chart describing the manner in which atrial arrhythmia preventive therapy may be delivered in accordance with the embodiment of FIG. 3.

Referring now to FIG. 5, it illustrates the therapy delivery subroutine 500 of FIG. 3. The process of FIG. 5 initiates at activity block 502 wherein preventive therapy is applied to the patient. The atrial arrhythmia preventive therapy, as previously described, may take the form of atrial overdrive pacing or the stimulation of extra-cardiac tissue. Such extra-cardiac tissue may be nerve tissue such as the stellate ganglia, the parasympathetic ganglia, or the central nervous system. Once the therapy is applied in accordance with activity block 502, the process advances to decision block 504. In decision block 504 it is determined if there is improvement in the monitored characteristic as for example, movement of the monitored characteristic towards a preset standard such as a baseline. If there has been no change or improvement in the monitored characteristic, the process advances to activity block 506 wherein the aggressiveness of the therapy is increased. Such increase in aggressiveness may take the form of increased stimulation amplitude, stimulation duration, or stimulation rate. Following the setting of the increased therapy in accordance with activity block 506, the process advances to decision block 508 wherein it is determined if the therapy has been set to a maximum limit. If the therapy has not been set to a maximum limit, the process then returns to activity block 502 for applying the therapy once again. However, if the maximum aggressiveness of the therapy has been reached, the process then proceeds to activity block 510 wherein the preventive therapy is terminated by returning the device to its regular parameters. Then, as can be seen in FIG. 3, the overall process proceeds to activity block 308 for the recording of the data associated with the identification of the impending accelerated atrial arrhythmia and the preventive therapy delivery.

If in decision block 504 it is determined that there has been an improvement in the monitored characteristic, the process then advances to decision block 512 where it is determined if the monitored characteristic has returned to baseline. If the monitored characteristic has not returned to baseline, the process then returns to activity block 502 for another application of the preventive therapy. However, if the monitored characteristic has returned to baseline, the process then advances to activity block 514 wherein the preventive therapy is continued for a set period of time. The duration of the therapy may be a programmable parameter of the device. Once activity block 514 is completed, the process then advances to activity block 510 wherein the device is returned to its regular parameters. Once again, following activity block 510, the overall process as shown in FIG. 3 advances to activity block 308 for the recording of the data associated with the identification of the impending accelerated atrial arrhythmia and the preventive therapy delivery.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. In a cardiac stimulation device, a system that identifies an impending atrial arrhythmia in a patient, the system comprising:
   a sensing circuit that senses atrial activity of a patient's heart including atrial T waves and provides corresponding atrial activity signals;
   memory that stores sensed atrial activity signals;
   a processor programmed to:
      detect accelerated atrial arrhythmias based on one or more atrial activity signal;
      upon detection of an accelerated atrial arrhythmia, create a template corresponding to the detected accelerated atrial arrhythmia using a feature of the atrial T waves included in a plurality of stored atrial activity signals sensed just prior to the detected accelerated atrial arrhythmia; and
      subsequent to template creation, compare at least one characteristic of a sensed atrial T wave to the template to identify an impending accelerated atrial arrhythmia; and
   a therapy circuit that is responsive to the processor identifying an impending accelerated atrial arrhythmia to provide atrial arrhythmia preventive therapy to the patient.

2. The system of claim 1 wherein the processor identifies an impending accelerated atrial arrhythmia when the at least one characteristic of the atrial T wave falls within the template.

3. The system of claim 1 wherein the processor is programmed to determine whether an atrial activity signal is an intrinsic signal or a paced signal and to create a first template corresponding to the atrial T waves included in intrinsic atrial activity and a second template corresponding to the atrial T waves included in paced atrial activity.

4. The system of claim 3 wherein the processor is programmed to classify the subsequently sensed atrial T wave as one of intrinsic activity or paced activity and to compare the sensed atrial T wave with a corresponding one of the first and second templates.

5. The system of claim 1 wherein the therapy circuit is arranged to provide high rate atrial pacing preventive therapy.

6. The system of claim 1 wherein the therapy circuit is arranged to provide high rate atrial pacing therapy to multiple atrial sites.

7. The system of claim 1 wherein the therapy circuit is arranged to provide stimulation pulses to extra-cardiac tissue.

8. The system of claim 1 wherein the therapy circuit is arranged to provide stimulation pulses to at least one of the stellate ganglia, the parasympathetic ganglia, and the central nervous system of the patient.

9. The system of claim 1 wherein the memory stores data associated with the impending accelerated atrial arrhythmia identification wherein the data includes time and date of each identification.

10. The system of claim 1 wherein the memory stores data associated with preventative therapy wherein the data includes duration of therapy.

11. The system of claim 1 wherein the memory stores data associated with the impending accelerated atrial arrhythmia identification wherein the data includes time between identification.

12. The system of claim 1 wherein the feature used to create the template and the characteristic compared to the template is atrial T wave amplitude.

13. The system of claim 1 wherein the feature used to create the template and the characteristic compared to the template is atrial T wave morphology.

14. A cardiac stimulation device comprising:
   sensing means for sensing atrial activity of a patient's heart including atrial T waves and providing corresponding atrial activity signals;
   memory that stores sensed atrial activity signals;
   processing means for:
      detecting accelerated atrial arrhythmias based on one or more atrial activity signal;
      upon detection of an accelerated atrial arrhythmia, creating a template corresponding to the detected accelerated atrial arrhythmia using a feature of the atrial T waves included in a plurality of stored atrial activity signals sensed just prior to the detected accelerated atrial arrhythmia; and
      subsequent to template creation, comparing at least one characteristic of a sensed atrial T wave to the template to identify an impending accelerated atrial arrhythmia; and
   therapy means responsive to the processing means identifying an impending accelerated atrial arrhythmia for providing atrial arrhythmia preventive therapy to the patient.

15. The device of claim 14 wherein the feature used to create the template and the characteristic compared to the template is atrial T wave amplitude.

16. The device of claim 14 wherein the feature used to create the template and the characteristic compared to the template is atrial T wave morphology.

17. In a cardiac stimulation device, a method of identifying an impending atrial arrhythmia in a patient, the method comprising:
   sensing atrial activity of a patient's heart including atrial T waves and providing corresponding atrial activity signal signals;
   storing sensed atrial activity signals;
   detecting accelerated atrial arrhythmias based on one or more atrial activity signal;
   upon detection of an accelerated atrial arrhythmia, creating a template corresponding to the detected accelerated atrial arrhythmia using a feature of the atrial T waves included in a plurality of stored atrial activity signals sensed just prior to the detected accelerated atrial arrhythmia;
   subsequent to template creation, comparing at least one characteristic of a sensed atrial T wave to the template to identify an impending accelerated atrial arrhythmia, and
   responsive to identifying an impending accelerated atrial arrhythmia, providing atrial arrhythmia preventive therapy to the patient.

18. The method of claim 17 and further comprising storing in a memory data associated with the impending accelerated atrial arrhythmia identification and preventive therapy delivery.

19. The method of claim 18 wherein the data includes time and data of each identification.

20. The method of claim 18 wherein the data includes duration of therapy.

21. The method of claim 18 wherein the data includes time between identification.

22. The method of claim 17 wherein an impending accelerated atrial arrhythmia is identified when at least one characteristic of the atrial T wave falls within the template.

23. The method of claim 17 wherein creating a template comprises determining whether an atrial activity signal is an intrinsic signal or a paced signal and creating a first template that corresponds to the atrial T waves included in intrinsic atrial activity and creating a second template that corresponds to the atrial T waves included in paced atrial activity.

24. The method of claim 23 wherein comparing further comprises classifying the subsequently sensed atrial T wave as one of intrinsic or paced activity and comparing the sensed atrial T wave with a corresponding one of the first and second templates.

25. The method of claim 17 wherein the therapy is high rate atrial pacing therapy.

26. The method of claim 17 wherein the therapy is high rate atrial pacing therapy to multiple atrial sites.

27. The method of claim 17 wherein the providing comprises providing stimulation pulses to extra-cardiac tissue.

28. The method of claim 17 wherein providing comprises providing stimulation pulses to the stellate ganglia of the patient.

29. The method of claim 17 wherein the feature used to create the template and the characteristic compared to the template is atrial T wave amplitude.

30. The method of claim 17 wherein the feature used to create the template and the characteristic compared to the template is atrial T wave morphology.

* * * * *